United States Patent [19]

Lingane et al.

[11] Patent Number: 5,885,839

[45] Date of Patent: Mar. 23, 1999

[54] METHODS OF DETERMINING INITIATION AND VARIABLE END POINTS FOR MEASURING A CHEMICAL REACTION

[75] Inventors: Paul J. Lingane, Redwood City; John F. Burd, San Diego; Karen A. Goins, San Diego; Michael D. Goins, San Diego, all of Calif.

[73] Assignee: LXN Corporation, San Diego, Calif.

[21] Appl. No.: 842,616

[22] Filed: Apr. 15, 1997

[51] Int. Cl.[6] .................................................. G01N 33/00
[52] U.S. Cl. ................................. 436/34; 436/46; 436/50; 436/67; 436/87; 436/93; 436/94; 436/95; 436/169
[58] Field of Search ................................. 436/34, 46, 50, 436/67, 87, 93–95, 169, 183

[56] References Cited

U.S. PATENT DOCUMENTS

| | | | |
|---|---|---|---|
| 4,199,261 | 4/1980 | Tidd et al. | 356/448 |
| 4,420,566 | 12/1983 | Jessop et al. | 436/46 |
| 4,637,403 | 1/1987 | Garcia et al. | 128/770 |
| 4,637,978 | 1/1987 | Dappen | 435/11 |
| 4,787,398 | 11/1988 | Garcia et al. | 128/770 |
| 4,956,301 | 9/1990 | Ismail et al. | 436/87 |
| 5,049,487 | 9/1991 | Phillips et al. | 436/46 X |
| 5,223,219 | 6/1993 | Subramanian et al. | 422/55 |
| 5,232,668 | 8/1993 | Grant et al. | 422/58 X |
| 5,316,727 | 5/1994 | Suzuki et al. | 422/68.1 |
| 5,344,754 | 9/1994 | Zweig | 436/46 X |
| 5,366,868 | 11/1994 | Sakamoto | 435/10 |
| 5,453,360 | 9/1995 | Yu | 435/28 |
| 5,470,752 | 11/1995 | Burd et al. | 436/87 |
| 5,597,532 | 1/1997 | Connolly | 422/58 |
| 5,725,774 | 3/1998 | Neyer | 422/56 X |

FOREIGN PATENT DOCUMENTS

| | | |
|---|---|---|
| 150965 | 8/1985 | European Pat. Off. . |
| 0 183 524 A2 | 11/1985 | European Pat. Off. . |
| 3707227 | 9/1987 | Germany . |
| 61-56943 | 3/1986 | Japan . |

OTHER PUBLICATIONS

D.B. Judd *Encycl. Ind. Chem. Anal.* 1966, 3, 376–392.

P.M.S. Clark et al, *Ann. Clin. Biochem.* 1983, 20, 208–212.

S.M. Marshall et al, *Diabetes care* 1983, 6, 543–547.

*Primary Examiner*—Arlen Soderquist
*Attorney, Agent, or Firm*—Campbell & Flores LLP

[57] ABSTRACT

The present invention provides a method of using a reflectance-reading device to determine an initiation time point for measuring the chemical reaction of an analyte from a biological liquid sample on a test surface. The initiation time point is determined by using a device to read a reflectance of a test surface at a plurality of time points, and calculating the K/S ratio of the test surface at each time point according to the Kubelka-Munk equation. As the device continues to calculate a K/S ratio for each time point, the device monitors the rate of change of the K/S ratio with respect to time. The device then determines the initiation time point to be when the rate of change of the K/S ratio is maximal. The present invention also provides a method of measuring the concentration of an analyte on a test surface. The concentration is measured by determining an initiation time point according to the method described above and then measuring the concentration of the analyte at a variable end point. The variable end point is essentially determined to be the time at which the rate of change of a concentration parameter is less than a threshold value.

16 Claims, 8 Drawing Sheets

Figure 1B
Rates of change of reflectance and K/S ratio over time: R' and (K/S)'
seconds after applying sample to test surface

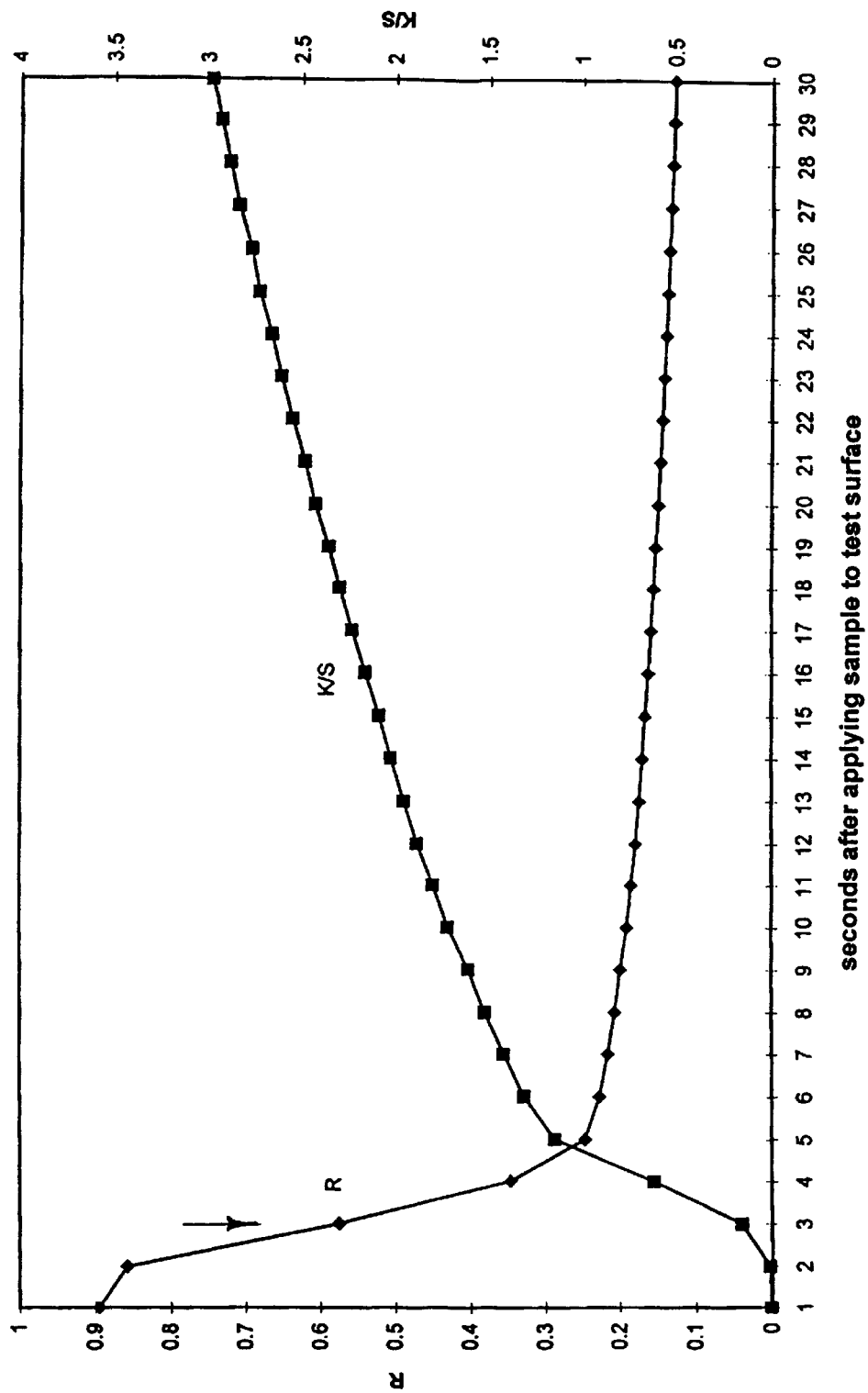

Rates of change of reflectance and K/S ratio over time: R' and (K/S)'

Fructosamine Strip
Reflectance and K/S ratio: R and K/S

Fructosamine Strip

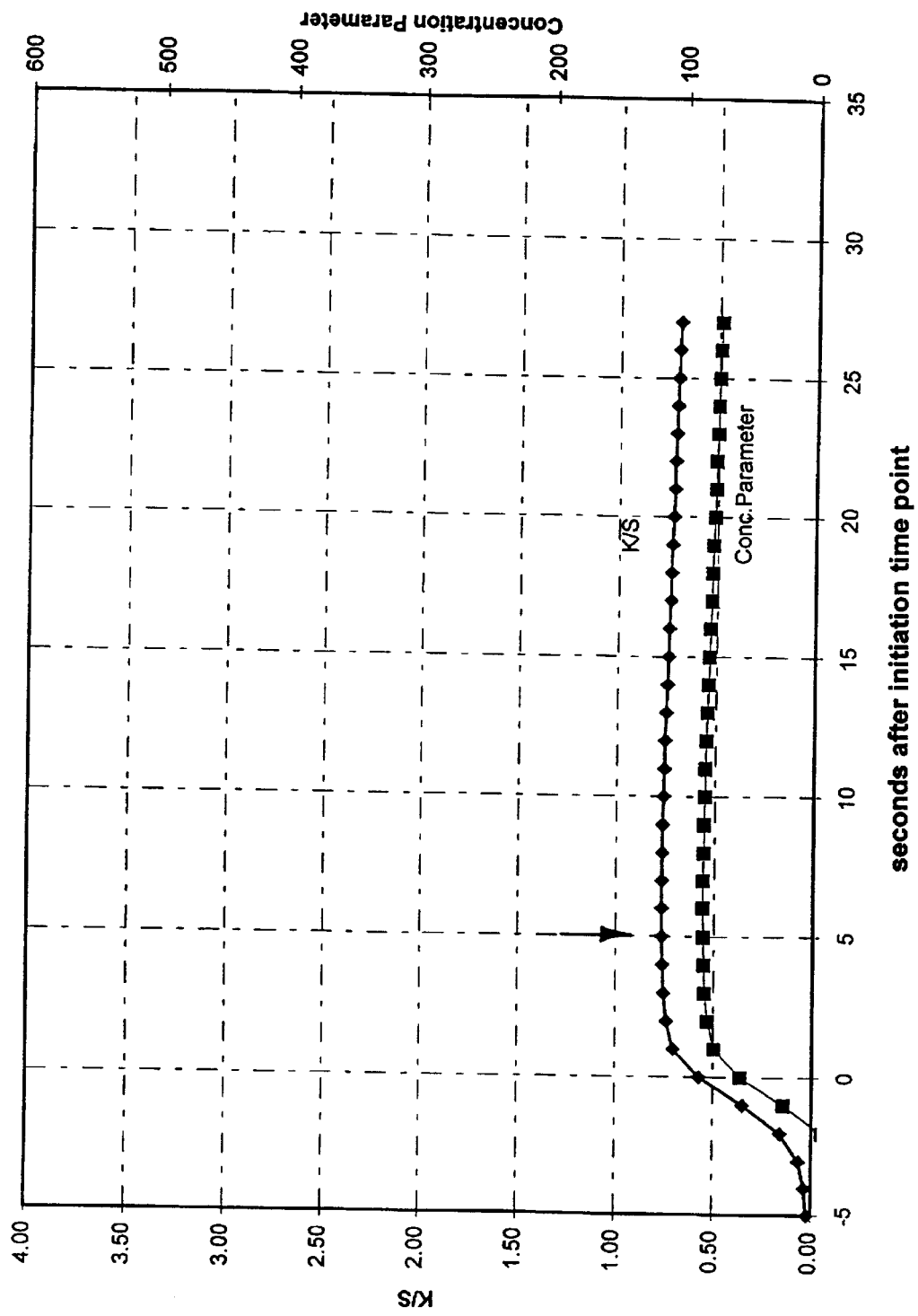

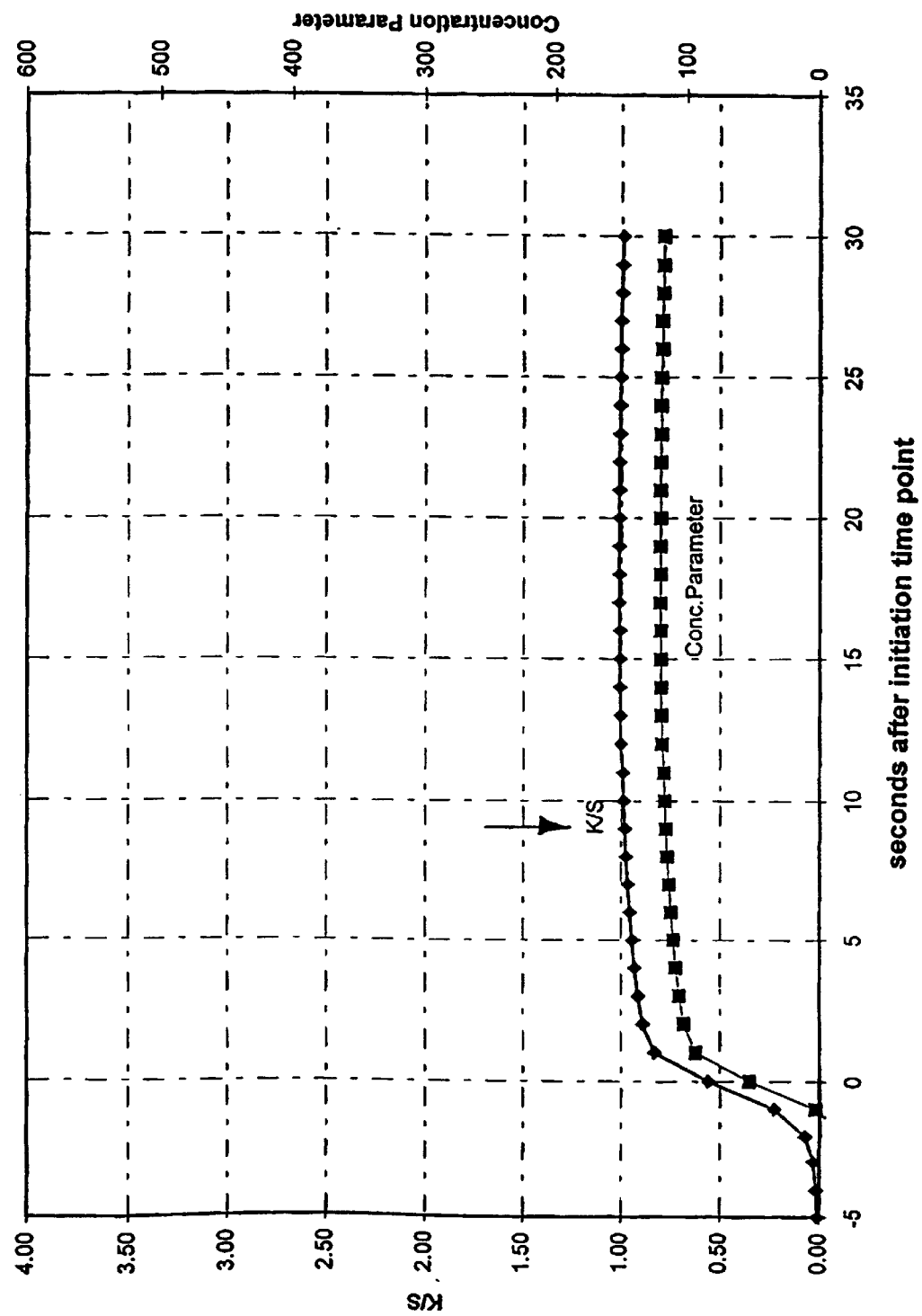

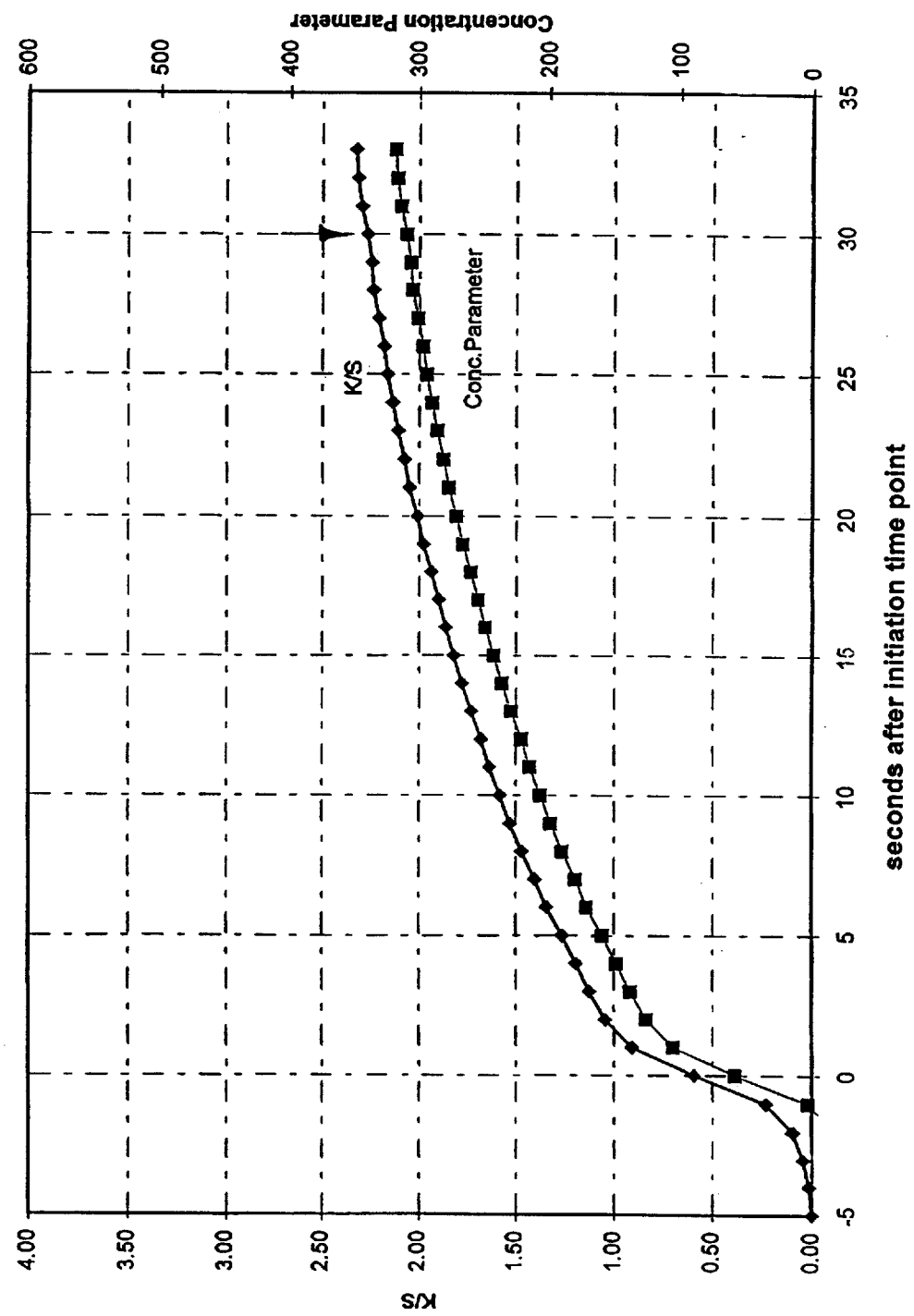

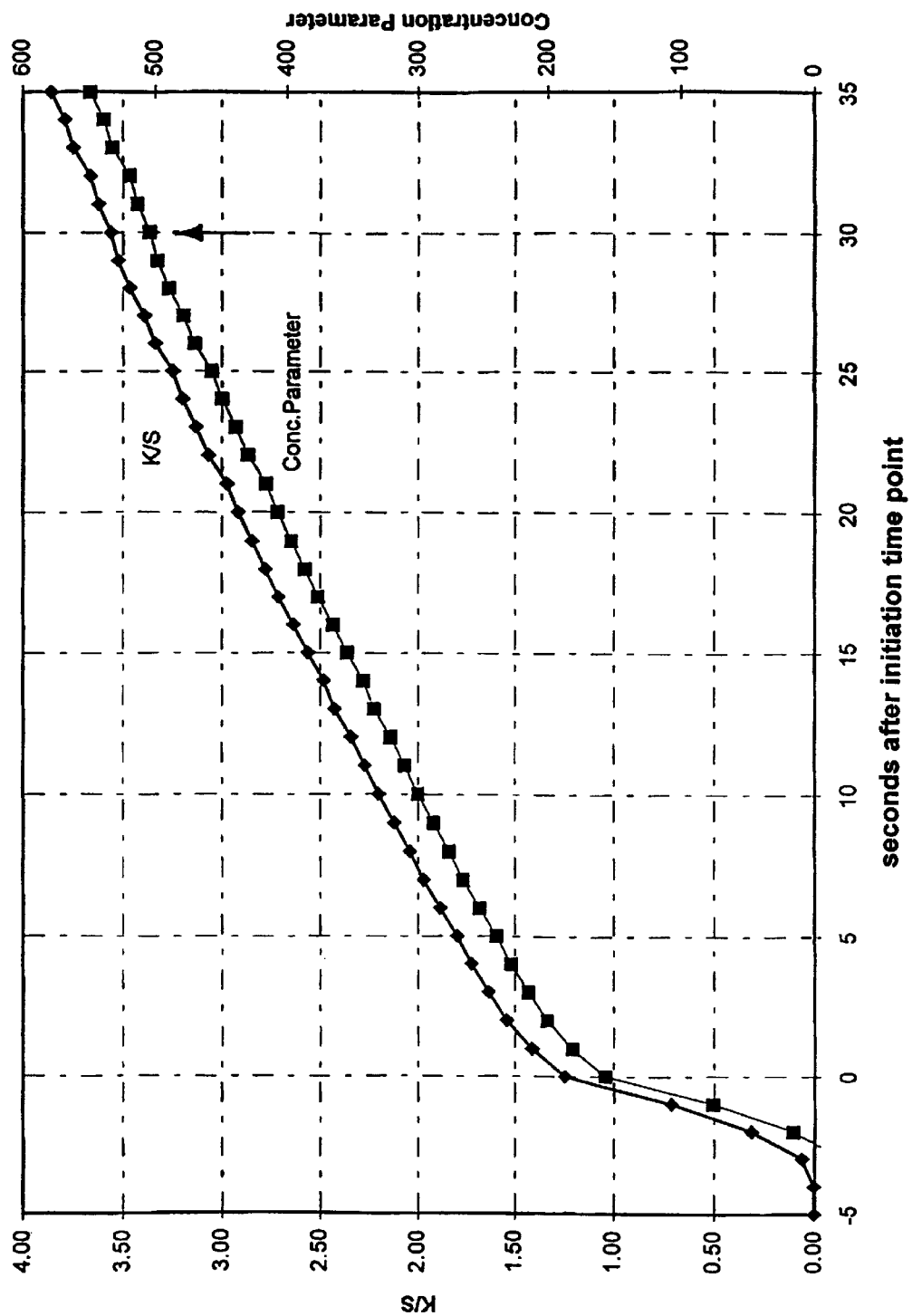

METHODS OF DETERMINING INITIATION AND VARIABLE END POINTS FOR MEASURING A CHEMICAL REACTION

BACKGROUND OF THE INVENTION

1. Field of the Invention

The present invention relates to automated methods of measuring chemical reactions. Specifically, the invention provides methods of using an automated reflectance-reading device to determine an initiation time point and a variable end point for measuring a chemical reaction.

2. Background Information

Patients with diabetes mellitus have an impaired ability to regulate glucose levels in their blood. As a result, diabetics can have abnormally high blood sugar levels known as hyperglycemia. Over time, chronic hyperglycemia may lead to long-term complications such as cardiovascular disease and degeneration of the kidneys, retinas, blood vessels and the nervous system. Studies indicate, however, that diabetics can substantially reduce such long-term complications by rigorously managing their blood sugar levels.

A significant part of diabetes management involves monitoring blood sugar levels. Depending on the nature and severity of an individual patient's disease, the patient's blood sugar levels can fluctuate throughout the day, so that some patients measure their blood sugar levels as often as seven times a day. Consequently, patients perform much of the monitoring themselves.

Several devices are available to allow diabetics to measure their blood sugar levels at home. To use such a device, a patient typically begins by inserting a test strip into the device. Some test strips have several layers, for example a top layer to receive a blood sample and filter red blood cells from the sample, an intermediate layer containing buffers to maintain the pH of the sample, and a bottom layer containing chemical reagents to react with the sample.

After inserting the test strip into the device, the patient then applies a blood sample to the strip. When a sample is applied to the top layer of a multilayer test strip, the sample must travel by wicking action through several layers before reaching the bottom layer where the chemical reaction can occur. The device monitors the chemical reaction occurring at the bottom of the test strip and subsequently displays a calculated measurement of the patient's blood sugar level. Because such critical measurements are often self-administered at home, the operation of the device must be easy-to-use, accurate and fast. Consequently, it is important that the device use a method for measuring a chemical reaction that is rapid without sacrificing accuracy.

Two important parameters of measurement methods used in home test devices are the initiation time point of the reaction and the end point of the reaction. The initiation time point is the time from which the device begins to measure the chemical reaction. The end point is the time at which the device determines that the chemical reaction is sufficiently complete to accurately calculate the patient's blood sugar measurement.

Some home test devices rely on essentially mechanical signals for determining the initiation time point. For example, one known device begins monitoring as soon as the test strip is inserted into the device. Another known device begins monitoring only after a door on the device is closed, enclosing the test strip within the device. Thus, how quickly a patient inserts the test strip or closes the device door after applying the blood sample can affect the initiation time point, and consequently affect the consistency and accuracy of the final measurement.

Other devices begin monitoring once they detect that the test strip has become wetted with the blood sample. With multilayer test strips, however, such a device may determine an initiation time point when it detects the wetting of the top layer, despite the delay between the wetting the top layer and when the sample reaches the bottom reagent layer to begin the chemical reaction. As a result, applying the initiation method of prior art devices to multilayer test strips may not accurately determine the actual starting time of the chemical reaction. Moreover, the starting time of the reaction may also be affected by the wicking properties of the individual layers, for example, variations in the thickness and porosity. Variations in the sample itself, for example, viscosity or sample volume can also affect wicking, resulting in inconsistent initiation time points.

Such home test devices also determine an end point of the chemical reaction based on a fixed time period after the initiation time point. Applying such methods to multilayer test strips may result in further variability: if the initiation time points are determined inconsistently, the fixed end points will also be determined inconsistently, resulting in potentially inaccurate blood sugar measurements.

Therefore, presently available methods for determining initiation and end points may yield inaccurate results when applied to multilayer test strips because they rely on signals or time periods unrelated to the behavior of the chemical reaction itself. Moreover, presently available methods can require an unduly prolonged time to provide a blood sugar measurement. While saving several seconds during each measurement may not appear significant at first, the time saved is substantial over several daily measurements for the entire course of a patient's diabetes management. Furthermore, an accurate device that saves a patient's time will encourage patients to monitor their blood sugar levels more regularly, thereby promoting compliance with their prescribed regimens for diabetes management.

The present invention satisfies the need for rapid and accurate determinations of initiation and end points for measuring a chemical reaction, and provides related advantages as well.

SUMMARY OF THE INVENTION

The present invention is directed to a method of using a reflectance-reading device to determine an initiation time point for measuring the chemical reaction of an analyte from a biological liquid sample on a test surface. The initiation time point is determined by using a device to read a reflectance of a test surface at a plurality of time points, and calculating the K/S ratio of the test surface at each time point according to the Kubelka-Munk equation. As the device continues to calculate a K/S ratio for each time point, the device monitors the rate of change of the K/S ratio with respect to time. The device then determines the initiation time point to be when the rate of change of the K/S ratio is maximal. In the initiation method of the invention, examples of the analyte are glucose and glycated protein such as fructosamine.

The present invention is also directed to a method of using a reflectance-reading device to measure the concentration of an analyte on a test surface. The concentration is measured by determining an initiation time point according to the method described above and then measuring the concentration of the analyte at a variable end point.

The variable end point is determined by using a device to read the reflectance of the test surface at a plurality of time points. For each time point, the device calculates a K/S ratio from the reflectance and then calculates a concentration parameter corresponding to the K/S ratio. As the device calculates the concentration parameter at each time point, the device monitors the rate of change of the concentration parameter with respect to time, comparing the rate of change of the concentration parameter with a threshold value. The device then determines the variable end point to be the time at which the rate of change of the concentration parameter is less than the threshold value. As a proviso, however, during a testing period that began at the initiation time point, if the rate of change of the concentration parameter is never less than the threshold value, then the variable end point is determined to be the end of the testing period. Subject to the proviso, the variable end point can also be determined to be the time at which the rate of change of the concentration parameter is less than the threshold value for two or more consecutive measurements of the rate of change of the concentration parameter. Exemplified values in the method of measuring concentration can be about 30 seconds for the testing period and 1% change of concentration parameter per second for the threshold value, where the analyte is glucose.

BRIEF DESCRIPTION OF THE DRAWINGS

FIGS. 1A and 1B illustrate the course of a chemical reaction over time for a sample containing approximately 450 mg/dL of glucose analyte. FIGS. 1A and 1C show the graphs of reflectance R (diamonds) and K/S (squares) over time. The x-axis is a time line measured in terms of seconds after applying a sample to the test surface. The arrows in FIGS. 1A and 1C indicate the initial drop in reflectance primarily due to wetting of the matrix by the biological liquid sample. FIGS. 1B and 1D show the corresponding graphs of the first derivatives of R (diamonds) and K/S (squares) with respect to time (R' and (K/S)', respectively). The arrows in FIGS. 1B and 1D indicate the initiation time point obtained by the initiation method of the invention. Further experimental details for FIGS. 1A to 1D are provided in Example I.

FIGS. 2A, 2B, 2C and 2D illustrate the course of chemical reactions in terms of K/S and concentration parameter over time, each for different concentrations of glucose analyte. FIGS. 2A, 2B, 2C and 2D correspond to glucose analyte concentrations of 88, 112, 300 and 500 mg/dL, respectively. The diamonds indicate K/S as measured by the left y-axis. The squares indicate the concentration parameter as measured by the right y-axis. The x-axis is a time line measured in terms of seconds after the initiation time point determined by the initiation method of the invention. The arrows indicate the variable end point used to measure the concentration of the glucose analyte according to the measurement method of the invention. Further experimental details for FIGS. 2A to 2D are provided in Example II.

DETAILED DESCRIPTION OF THE INVENTION

Figure 1B:
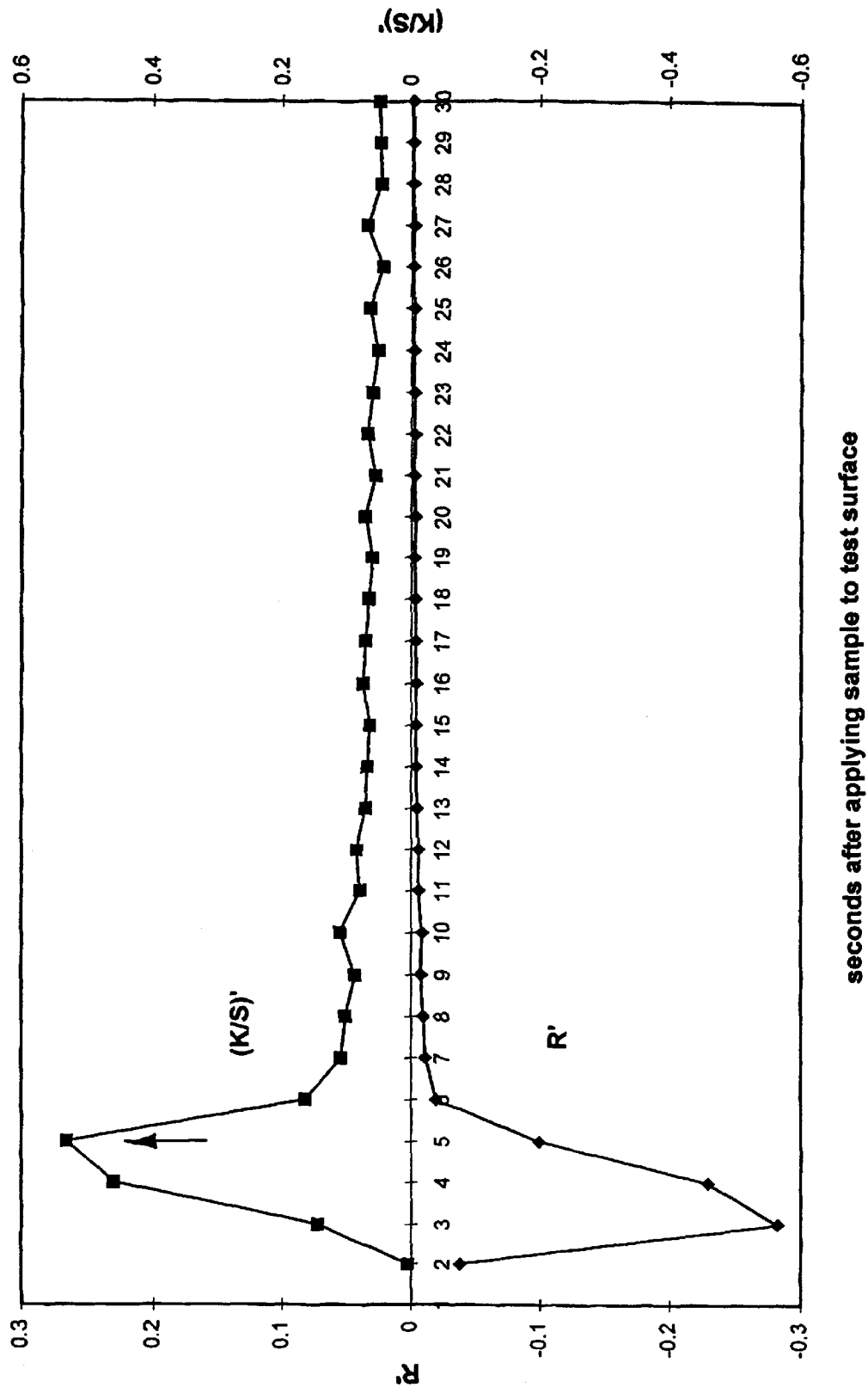

The present invention is directed to a method of using a reflectance-reading device to determine an initiation time point for measuring the chemical reaction of an analyte in a biological liquid sample on a test surface. The term "initiation time point," is used herein to mean the time from which the device begins to measure the chemical reaction. The initiation time point is determined by using a device to read a reflectance of a test surface at a plurality of time points, and calculating the K/S ratio of the test surface at each time point according to the Kubelka-Munk equation. As the device continues to calculate a K/S ratio for each time point, the device monitors the rate of change of the K/S ratio with respect to time, which can be rephrased as the first time derivative of the K/S ratio or (K/S)'. The device then determines the initiation time point to be when the rate of change of the K/S ratio (K/S)' is maximal, meaning at its greatest value relative to values at other time points.

As disclosed, the present invention generally relates to methods of using a device to read the reflectance of a test surface. Such devices are well known in the art, and typically direct light toward a test surface. The light can be of a specific wavelength, such as that from a light-emitting diode. The test surface then scatters the incident light in other directions, termed "diffuse reflectance." The diffuse reflectance from the test surface is monitored by an optical detector, which can be coupled to a microprocessor or other means for mathematically processing the detector signal for further use. Thus, as used herein, a "reflectance-reading device" is an apparatus that can measure the diffuse reflectance of light from a test surface.

The test surface itself is typically located on a disposable test strip to be inserted into the device, but can be any surface from which the device reads diffuse reflectance. A test strip can also comprise several layers, where the exposed surface of the bottom layer is the test surface to be read by the device. The test surface comprises in part a matrix, such as a hydrophilic porous matrix. If a biological liquid sample is applied to the matrix, the matrix will incorporate some of the sample by wetting or saturation. The matrix can also incorporate a chemical reagent selected to react with the analyte of interest. For example, the matrix can be pretreated with the chemical reagent, or the chemical reagent can be carried from a reagent-containing layer to the matrix by the wicking action of the liquid sample as it saturates each layer of a stack. As a result, the diffuse reflectance properties of the test surface as a whole can involve the diffuse reflectance properties of each component of the test surface. Therefore, as used herein, the term "test surface" means the combination of the matrix, any biological liquid sample wetting or saturating the matrix and any chemical reagent present on the matrix.

The "biological liquid sample" to be applied to the matrix of the test surface encompasses any body fluid containing an analyte to be measured. For example, the term encompasses blood, serum or plasma. The term also encompasses other patient specimens such as cerebral fluid, saliva, semen, spinal fluid, sputum, tears, urine and cervical mucus or swabbings. The term further encompasses food, environmental or industrial samples as long as they are liquid, of biological origin and contain an analyte for measurement.

The "analyte" in the biological liquid sample can be any substance to be detected or quantitated in terms of concentration. For example, the analyte can be glucose, fructose, or other sugars, cholesterol, ketones, lipids, uric acid or specific amino acids such as phenylalanine. The analyte can also be proteins, for example, enzymes such as amylase, creatine kinase or alanine aminotransferase. Furthermore, the analyte can be glycated proteins, for example serum or plasma glycated protein as measured by fructosamine, or red blood cell glycated protein as measured by glycated hemoglobin, in particular, $Hb_{A1C}$. Analytes useful in the method of the invention are described in U.S. Pat. No. 5,597,532 to Connolly, which is incorporated herein by reference.

The analyte to be measured will direct the selection of an appropriate chemical reagent. As used herein, the "chemical reagent" is any chemical or combination of chemicals that react with an analyte to produce a change in the reflectance of the test surface. If the analyte is glucose, for example, the chemical reagent can be a chromophore selected to develop a color in the presence of glucose, thereby changing the reflectance of the test surface. Chemical reagents for reacting with an analyte are well known in the art, for example the tetrazolium dyes used to react with fructosamine described in U.S. Pat. No. 5,470,752 to Burd et al., which is incorporated herein by reference. Several other such chemical reagents, which can react with an analyte to result in a change in the reflectance of the test surface, are described in previously cited U.S. Pat. No. 5,597,532 to Connolly.

The change in the reflectance values from the chemical reaction can be mathematically related to the concentration of the analyte by the work of Paul Kubelka and Franz Munk. Their work used the ratio K/S to analytically describe the relationship between color development according to the optical absorbance K of liquid dye and diffuse reflectance according to the scattering coefficient S of a surface containing the dye. As the scattering coefficient S decreases, for example when a test surface becomes wetted, less light becomes scattered by the test surface so that less light reaches the optical detector, thereby raising the value of the K/S ratio. In addition, as the color on a test surface becomes darker, for example due to a chemical reaction, the optical absorbance K increases, thereby also causing the K/S ratio to increase. Consequently, the K/S ratio can be directly related to color development and inversely related to the light scattering of a test surface.

Kubelka and Munk derived several formulas describing the relationship between diffuse reflectance and the K/S ratio, which are well known in the art and are described, for example, in D. B. Judd and G. Wyszecki, *Color in Business, Science, and Industry* (John Wiley & Sons, New York (1975)), which is incorporated herein by reference. Several of the formulas derived by Kubelka and Munk can be applied in the present invention, depending on the optical details of the device and the properties of the test surface.

In one of the simpler approximations derived by Kubelka and Munk, the test surface is considered optically thick so that any further increase in thickness does not significantly affect its reflectance. In this approximation, the ratio K/S is related to the reflectance R of the test surface according to the equation $$K/S = (1-R)^2/2R$$

This formulation of K/S is the Kubelka-Munk parameter, which mathematically relates reflectance readings to chemical processes, such as the concentration of the analyte on the test surface. In essence, the work of Kubelka and Munk links the photometric world of instrumentation with the chemical world of the test surface. As a result, the K/S ratio is useful for determining an initiation time point based on the kinetics of the chemical reaction over time.

As disclosed, the device reads the reflectance of the test surface at a plurality of time points, meaning at least two time points. At each time point, the device then calculates the K/S ratio, which can be related to the kinetics of the chemical reaction. In terms of reflectance and K/S, a paradigmatic chemical reaction measured by the device is shown in FIG. 1A and can be described as follows:

(a) Before applying the biological liquid sample to the test strip, the reflectance of the test surface is relatively high and the K/S ratio is relatively low.

(b) When the sample is applied to the test strip, the reflectance decreases a certain amount primarily due to wetting of the matrix by the sample, typically 5%–50%. The drop in reflectance can be interpreted as a decrease in the scattering coefficient S, which raises the K/S ratio. Despite the change in the K/S ratio, however, the chemical reagent may not have begun to react with the analyte in the sample. See FIG. 1A at the 3 second mark.

(c) When the chemical reagent begins to react with the analyte in the sample, the color begins to develop, resulting in a rise in the optical absorbance K. Consequently, the K/S ratio increases further.

(d) As the chemical reaction progresses, the K/S ratio continues to increase.

Thus the behavior of the K/S ratio over time depends not only on the chemical reaction, but also on wetting of the matrix, which is a physical process not directly related to the chemistry of the reaction. Consequently, the initiation time point must be determined appropriately to yield an accurate measurement.

Figure 1C:
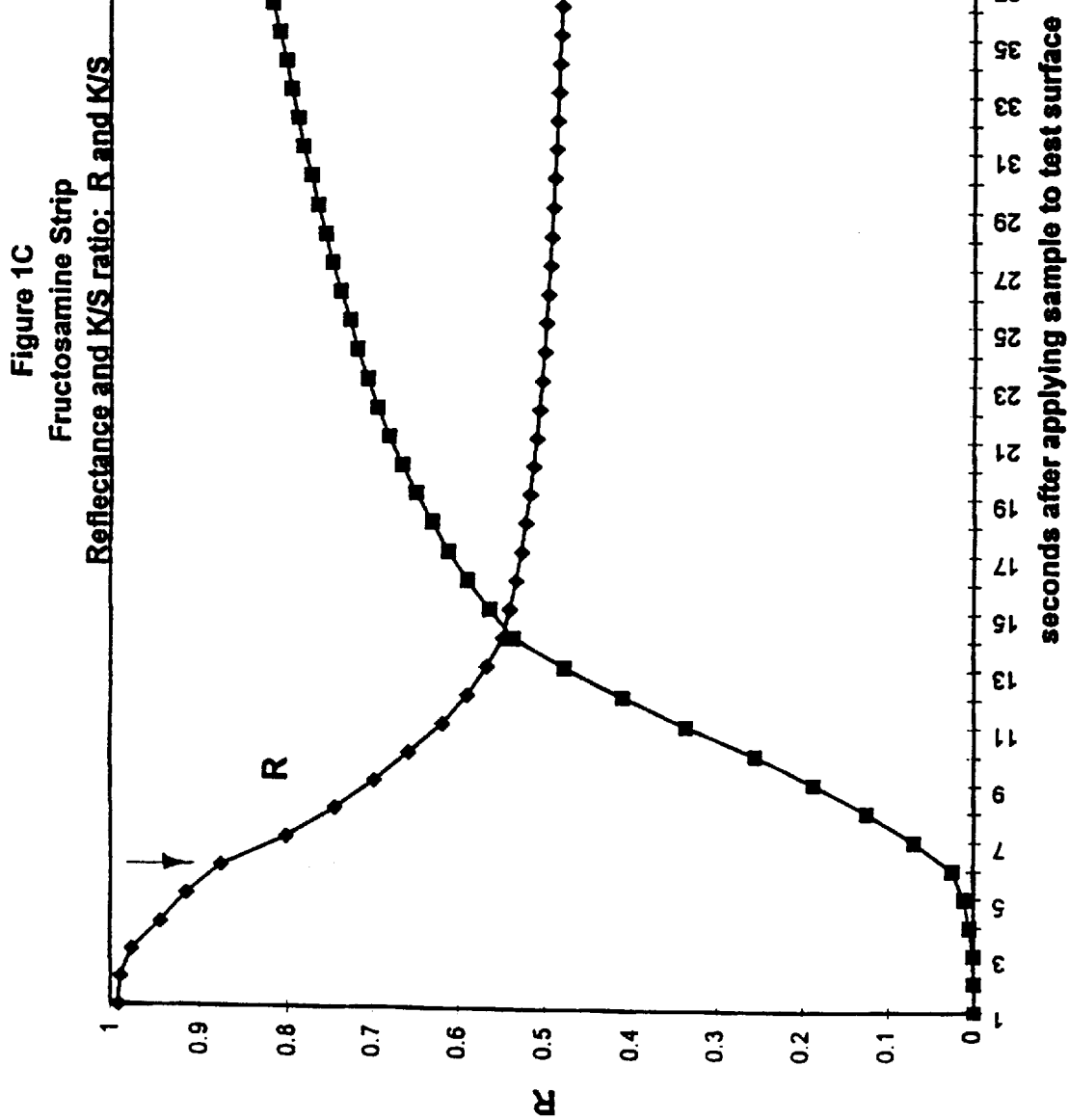
FIGS. 1C and 1D illustrate a similar course for a fructosamine sample at approximately 187 $\mu$M.
Figure 1D:
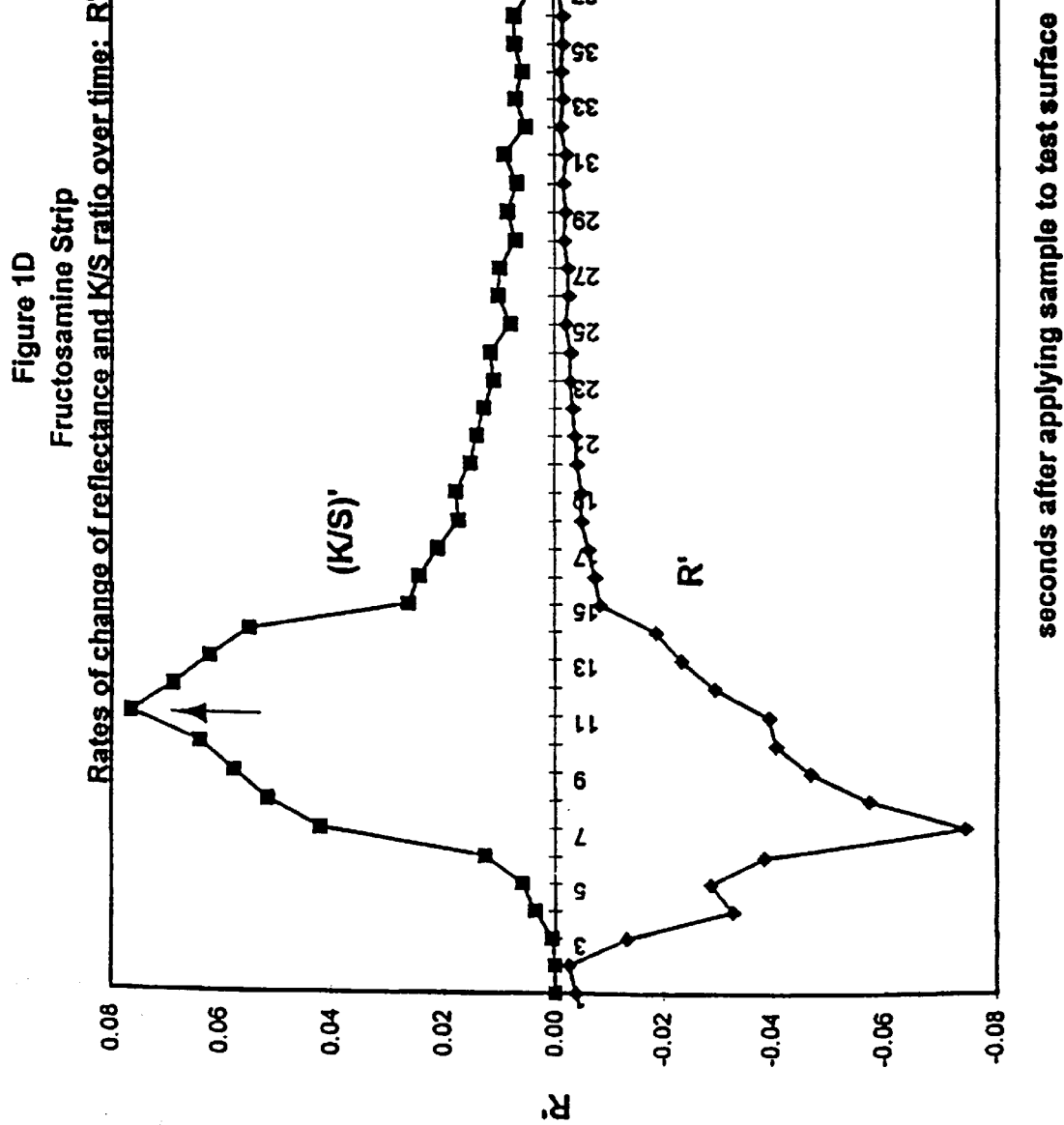

As disclosed, the initiation method of the invention is illustrated in FIGS. 1A and 1B. FIG. 1A shows the course of reflectance and the K/S ratio during a chemical reaction. FIG. 1B shows the corresponding values for the first time derivative of reflectance R' and the first time derivative of the K/S ratio (K/S)'. As shown in FIG. 1A, it may appear that the reflectance values and the K/S ratio have an approximately inverse relationship. This is not the case: because the relationship between R and K/S is nonlinear, the maximum for (K/S)' does not necessarily occur at the same time as the minimum for R'. According to the kinetics of the chemical reaction shown in FIGS. 1A and 1B, the value of (K/S)' reaches a maximal value at 5 seconds after applying the sample to the test strip. Consequently, the method of the invention determines the initiation time point to be at 5 seconds. Similarly, FIGS. 1C and 1D illustrate the determination of an initiation time point at 11 seconds for a reaction measuring fructosamine. Thus, the method of the invention determines an initiation time point according to the kinetics of the chemical reaction itself.

The initiation method of the invention contrasts with other methods used in the prior art, which determine the initiation time point from essentially mechanical signals unrelated to the kinetics of the chemical reaction. One prior art device determines an initiation time point when the test strip is inserted into the device. Another prior art device begins monitoring as soon as a door on the device is closed, enclosing the test strip within the device. The initiation time point obtained by such methods, however, is unrelated to the actual start of the chemical reaction. Thus, such devices cannot ensure that a user will obtain consistent or accurate measurements.

Other prior art devices, such as those described in U.S. Pat. No. 5,049,487 to Phillips et al., determine initiation time points by detecting an initial drop, for example of 10%, in the reflectance of the test surface. As discussed above, when a sample is applied to the test strip, the air in the matrix is replaced with liquid sample as the matrix becomes wetted, resulting in a measurable decrease in reflectance. This initial change in reflectance occurs simply by wetting the matrix, even though the chemical reagent may not yet have begun to react with the analyte. For example, in FIG. 1A, a 10% drop in reflectance occurs at 3 seconds after applying the sample, compared to an initiation time of 5 seconds obtained by the method of the invention. Similarly, a 10% drop in reflectance occurs at 6 seconds in FIG. 1C, compared to the initiation time of 11 seconds shown in FIG. 1D.

The delay between wetting the matrix and the starting the chemical reaction is especially significant when the test strip contains a stack of membranes, for example as described in previously cited U.S. Pat. No. 5,470,752 to Burd et al. For example, a biological liquid sample can be applied at the top of a stack where the sample saturates the top layer, migrates through the intervening layers, then reaches the bottom of the stack, which serves as the test surface for reading the reflectance. When the sample is applied at the top of the stack, the wetting of the top the stack may cause a detectable change in reflectance, which may trigger an initiation time point in the prior art methods. However, 10 to 20 seconds may elapse before the sample actually reaches the chemical reagent at the bottom of the stack, thereby starting the actual chemical reaction. Consequently, the methods used by prior art devices may initiate measurement of the chemical reaction prematurely.

The delay between wetting the matrix and starting the chemical reaction may also vary because of other factors. For example, the thickness and porosity of the individual layers of the test strip may vary because of manufacturing constraints, causing some variation in the time required for the sample to migrate from the top to the bottom layer. The delay may also vary because the blood sample itself varies between measurements, for example, the viscosity or the volume of the sample applied.

Yet another prior art device, described in U.S. Pat. No. 5,344,754 to Zweig, determines when a sample is applied to the matrix when it detects a change in the electrical conductivity of the matrix. Like the preceding prior art devices, the method used in this prior art device is also inadequate to determine the initiation point of a chemical reaction because it merely determines when the sample was added, not when the chemical reaction begins. As a result of using the reaction kinetics, the initiation method of the invention provides more accurate measurements than the methods used in the prior art, as shown in Example III.

The benefits of using reaction kinetics extend to other methods of measuring a chemical reaction such as determining the end point of the reaction and measuring the concentration of the analyte. Once a chemical reaction has started, the behavior of the K/S ratio can vary according to the nature of the chemical reaction, for example the identity and concentration of the components of the reaction, as well as ambient conditions such as temperature and humidity. In some reactions, termed "rate" reactions, the K/S ratio continues to increase over time at a certain rate, which can also be directly related to the concentration of the analyte.

In other reactions, termed "end point" reactions, the K/S ratio increases over time until it attains and remains at a final value, which can be directly related to the concentration of the analyte. In such reactions, however, the user need not wait for the K/S ratio to reach a final value to obtain an accurate concentration measurement. Instead, the K/S ratio can be measured at a carefully selected end point so that the K/S ratio at that end point can be accurately related to a concentration of the analyte. As a result, an accurate concentration measurement can be obtained more quickly than if the reaction were allowed to continue until the K/S ratio reached its final value. Because the end point is not determined from a fixed time period, it is termed a "variable" endpoint.

For example, the K/S ratio in FIG. 2B essentially reached its final value 9 seconds after the initiation time point. Similarly, the K/S ratio in FIG. 2A reached an endpoint at 5 seconds. It should be noted that under some circumstances, for example in FIG. 2A, the K/S may reach a certain value, maintain that value for a certain period, and then begin to drop again, perhaps due in part to external conditions unrelated to the chemical reaction itself, such as evaporation. Thus, in FIG. 2A, K/S began to decline after 7 seconds.

The present invention is therefore directed to a method of using a reflectance-reading device to measure the concentration of an analyte on a test surface. The concentration is measured by determining an initiation time point according to the initiation method of the invention as described above and then measuring the concentration of the analyte at a variable end point. As used herein, the "end point" is the time at which the device determines that the chemical reaction is sufficiently complete to accurately calculate the concentration of the analyte.

The variable end point is determined by using a device to read the reflectance of the test surface at a plurality of time points. For each time point, the device calculates a K/S ratio from the reflectance and then calculates a concentration parameter corresponding to the K/S ratio. As the device calculates the concentration parameter at each time point, the device monitors the rate of change of the concentration parameter with respect to time, comparing the rate of change of the concentration parameter with a threshold value. The device then determines the variable end point to be the time at which the rate of change of the concentration parameter is less than the threshold value. As a proviso, however, during a testing period that began at the initiation time point, if the rate of change of the concentration parameter is never less than the threshold value, then the variable end point is determined to be the end of the testing period.

Related methods of determining the variable end point can also be used in the measurement method of the invention. For example, the variable end point can be determined to be the time at which the rate of change of the concentration parameter is less than the threshold value for two or more consecutive measurements of the rate of change of the concentration parameter. In addition, the variable end point can be determined to be the time at which the rate of change of the K/S ratio, not the concentration parameter, is less than a threshold value for one or more consecutive measurements. Both related methods can be subject to the proviso, and are comparably equivalent to the measurement method of the invention described in greater detail below.

As used herein, the term "concentration parameter" or $C_t$ means a value calculated from the K/S ratio at each time point t according to a calibration curve. The calibration curve is prepared so that if the K/S ratio were at an end point, then the value of the concentration parameter is be equal to the concentration of the analyte. Those skilled in the art can readily calibrate a linear, piecewise linear or higher order polynomial curve by measuring the K/S ratios resulting from a predetermined series of control samples according to the measurement method of the invention. It follows that the change in the concentration parameter over time can also be calculated and is represented by $C_t'$.

The concentration parameter is illustrated in FIG. 2D, where $C_t$ has a value of 300 mg/dL at 10 seconds, 408 mg/dL at 20 seconds, 505 mg/dL at 30 seconds and 550 mg/dL at 35 seconds after the initiation time point. Because 30 seconds is determined to be the end point, the value of $C_t$ is equal to the actual concentration of the analyte. As illustrated in FIG. 2D, however, the value of $C_t$ changes over the course of a reaction because it is calculated from the changing values of reflectance over time as read by the device.

As used herein, the term "threshold value" or $C_k'$ refers to a set rate of change of the concentration parameter to be compared to the rate of change of the concentration parameter $C_t'$ at a given time point. Depending on the nature of the chemical reaction, the threshold value can be about 1%, so that as used herein, "about 1% " encompasses a range between 0.5% and 1.5%. The threshold value can also be any value between 0.1% and 10% such as 0.1%, 0.2%, 0.5%, 1%, 2%, 5% or 10%.

The term "testing period" or $T_k$ means a fixed time during which the end point is determined. The testing period begins at the initiation time point $T_i$ determined by the initiation method of the invention, and can be about 30 seconds, so that as used herein, "about 30 seconds" encompasses a range between 15 seconds and 35 seconds. Depending on the nature of the chemical reaction, the testing period can also be any value from 10 seconds to 100 seconds, for example, 10 seconds, 20 seconds, 40 seconds, 60 seconds, 80 seconds or 100 seconds.

Suppose by way of example that the exemplified values for the threshold value $C_k'$ is 1% and the testing period $T_k$ is 30 seconds. If the rate of change of the concentration parameter is less than 1% per time, then the endpoint is determined to be the time when the rate of change of the concentration parameter is less than 1%. In FIG. 2B, for example, the rate of change of the concentration parameter during the period between 8 and 9 seconds was less than 1%, so the end point was determined to be at 9 seconds, resulting in a concentration measurement of 116 mg/dL.

Alternatively, if the rate of change of the concentration parameter is never less than 1% for each time point, then the end point is determined according to the proviso to be the end of the testing period. In FIG. 2D, for example, the rate of change during the testing period from 0 to 30 seconds was never less than 1%. Therefore, the end point was determined to be at 30 seconds, yielding a concentration measurement of 505 mg/dL.

To formulaically summarize the method of determining the variable end point:

for each successive t between $T_i$ and $T_i+T_k$:
  if $C_t'<C_k'$ for the time interval t−1 to t, then the end point is at t;
  but if $C_t' \not< C_k'$ between $T_i$ and $T_i+T_k$, then the end point is at $T_i+T_k$.

As disclosed, the measurement method of the invention provides the advantage of providing a rapid, yet accurate measurement of the analyte concentration. One prior art device, described in U.S. Pat. No. 5,366,868 to Sakamoto, uses a predetermined time of 5 to 7 minutes after the incubation of the chemical reaction begins. Another prior art device, described in U.S. Pat. No. 5,049,487 to Phillips et al., uses a predetermined time of 20 or 30 seconds after a certain initiation time point to determine the end point for measuring the analyte concentration. Such methods can require an unduly prolonged time to obtain an accurate measurement.

For example, in FIG. 2A, the prior art method described in the patent to Phillips et al. would provide a measurement roughly at 20 to 30 seconds, depending on when the prior art device determined the test surface had become wetted. Significantly, when this prior art method is used with multilayer strips, the method may provide a misleadingly low measurement if it takes its measurement while the reflectance is declining due to physical rather than chemical factors. In contrast, the method of the invention can provide a rapid measurement that is more consistent, as shown in Example III.

Although the methods described in this application are particularly directed to measuring glucose and fructosamine with multilayer test strips, there is no need to limit the application of the initiation and measurement methods of the invention to such analytes and test strips, the breadth of which are discussed above. Thus, the following examples are intended to illustrate, but not limit the present invention.

EXAMPLE I

Determination of an Initiation Time Point for Measuring a Chemical Reaction

The following example illustrates the initiation method of the invention as applied to reactions measuring glucose, as shown in FIGS. 1A and 1B, and fructosamine, as shown in FIGS. 1C and 1D.

A. Initiation Time Point for Glucose Reaction

A sample containing 450 mg/dL glucose was prepared by allowing a whole blood sample to metabolize to a value less than 50 mg/dL, then spiking the sample with a concentrated glucose solution. The final glucose concentration of the sample was verified by a YSI Stat-2300 Glucose Analyzer (Yellow Springs Instruments Inc., Yellow Springs, Ohio).

The sample was applied to a test strip that contained two layers of membrane material situated in fluid communication with each other. The upper layer was a nonwoven polyester layer that can separate cells from plasma, allowing the plasma to migrate to the lower layer. The lower layer was a nylon membrane with a 0.65 μm pore size and impregnated with chemical reagents. The chemical reagents were a glucose oxidase/horseradish peroxidase system (Toyobo Inc., Tokyo, Japan) with a N-ethyl-N-(2-hydroxy-3-sulfopropyl)-m-toluidine (TOOS) color indicator (Research Organics Inc., Cleveland, Ohio), both of which are well known in the art for quantitating glucose concentration.

Once the sample was applied to the test strip, the reflectance of the test strip was measured over time. A light-emitting diode (LED) directed light having a wavelength of 635 nm to the surface of the test strip. At one second intervals, the diffuse reflected light was detected by a silicon photodiode, which generated an analog signal. The signal was then processed by a tranfsconductance amplifier, a synchronous detector, an analog to digital converter and a micoprocessor. Automated processing and analysis of such detector signals is well known in the field of medical devices (see, for example, U.S. Pat. No. 5,597,532 to Connolly). The microprocessor controlled the timing of the reflectance measurements and relayed the measurements to a personal computer where they were analyzed to yield values for the reflectance, the K/S ratio and the concentration parameter.

FIG. 1A charts the course of the chemical reaction over time in terms of reflectance (diamonds) and the K/S ratio (squares). The x-axis is a timeline measured in terms of seconds after applying the sample to the test surface. The course of the reflectance was initially high (near a value of 1), but rapidly decreased after the sample was applied. The early decrease between 2 and 3 seconds can be attributed in part to the wetting of the test surface by the sample. The K/S ratio was calculated from the reflectance value R according to the Kubelka-Munk formula $K/S=(1-R)^2/2R$. The course of the K/S ratio shows an initial rapid rise and then a steady increase over time.

FIG. 1B illustrates the course of the first time derivatives of reflectance and the K/S ratio (R' and K/s', respectively). According to the initiation method of the invention, the initiation time point is determined to be when K/S' is maximal. Here, K/S' was maximal at the 5 second mark, marked by the arrow. Thus, in this chemical reaction, the initiation time point was determined to be at 5 seconds.

B. Initiation Time Point for Fructosamine Reaction

The initiation time point for a fructosamine reaction was determined essentially as described above in Example I.A, with the following modifications.

The whole blood sample was spiked with glycated human serum albumin and the final concentration of 187 µM was verified using the Roche Unimate reagent (Roche Diagnostic Systems, Totowa, N.J.) as determined by a Cobas Fara system (Roche Diagnostics Systems, Montclair, N.J.). The instrumentation was the same as for the glucose reaction, except the LED-emitted light is at a wavelength of 565 nm.

The sample was applied to a multilayer fructosamine test strip as essentially described in U.S. patent application Ser. No. 08/418,523, published as PCT WO 96/31270, both of which are incorporated herein by reference. There were three minor modifications to the fructosamine test strip used in this example, as follows. First, rather than a single layer of Blood Separation Matrix, the test strip used two layers of the matrix. Each layer was treated with a solution containing between 0.0001% and 0.1% Pluronic detergent (Pragmatics Inc., Oak Ridge, Tenn.), 8% mannitol and 0.15% hexadimethrine bromide in a 0.85% NaCl saline solution. Second, the BTS polysulfone membrane (Memtek Inc., San Diego, Calif.) was part number BTS-15. Third, an additional Whatman Glass Fiber layer grade F165 (Whatman Inc., Clifton, N.J.) was interposed between the Buffer Layer and the Dye Layer.

An arrow in FIG. 1C indicates a 10% decrease in reflectance at 6 seconds, which can be attributed in part to the wetting of the test surface by the sample. In this fructosamine reaction, the initiation time point was determined to be at 11 seconds, which is when K/S' was maximal, as indicated by the arrow in FIG. 1D.

EXAMPLE II

Measurement of the Concentration of an Analyte Using an Initiation Time Point and Variable End Point The following example illustrates the measurement of analyte concentration by the initiation and variable end point methods of the invention.

As a preliminary step, a standard curve was calibrated to correlate K/S ratios calculated from the reflectance-reading device to the concentration of glucose in the sample. Whole blood samples were prepared as described in Example I.A at glucose concentration levels between 20 mg/dL to 600 mg/dL. The samples were applied to test strips, and the reflectance and K/S ratios of the test strips was measured over time as described in Example I.A. The mean endpoint values for K/S were determined for each concentration essentially according to the measurement method of the invention.

TABLE I

Calibration between K/S and glucose concentration

| Mean endpoint K/S ratio | Glucose concentration (mg/dL) |
|---|---|
| 0.3434 | 20 |
| 0.7419 | 80 |
| 1.2068 | 150 |
| 1.8710 | 250 |
| 2.5352 | 350 |
| 3.1994 | 450 |
| 4.1957 | 600 |

The mean endpoint K/S values were used to plot a piecewise calibration curve of 6 linear segments to correlate K/S values with glucose concentrations. The curve was subsequently used to calculate a concentration parameter corresponding to a K/S ratio at any time point during a chemical reaction.

The glucose concentration of four whole blood samples were then measured according to the method of the invention as follows. Whole blood samples were prepared as described in Example I.A at glucose concentrations of approximately 88, 112, 300 and 500 mg/dL. In brief, the samples were applied to test strips, and the initiation time point was determined according to the method of the invention as described in Example I.A. Second, the glucose concentration of the sample was determined to be the value of the concentration parameter at the variable end point, which was determined as described in further detail below.

For the 112 mg/dL sample shown in FIG. 2B, the variable end point was determined as follows. First, the reflectance of the test strip was measured at 1 second intervals. Second, the corresponding K/S ratio was determined from the reflectance measurement at each time point. Third, a concentration parameter was calculated from the K/S ratio according to the calibration curve described above. Fourth, the rate of change of the concentration parameter over time $C_t'$ was calculated for each time point and monitored over the course of the reaction.

Fifth, the value of the rate of change of $C_t$ ($C_t'$) at each time point was compared against a threshold value of 1%. For example, in FIG. 2B, the rate of change for $C_t$ at 8 seconds after the initiation time point was 1.2% change per second ($C_t'$ measured between 7 seconds and 8 seconds after the initiation time point). At 9 seconds after the initiation time point, the value for $C_t'$ was about 0.9% change per second ($C_t'$ measured between 8 seconds and 9 seconds after the initiation time point). Sixth and finally, because the value of $C_t'$ at 9 seconds was less than 1%, the variable end point was determined to be at 9 seconds in this reaction. Consequently, the concentration was determined to be 116 mg/dL, which was the concentration parameter at 9 seconds after the initiation time point (indicated by the arrow). The measurement of the 88 mg/dL sample, as shown in FIG. 2A, proceeded in the same way, except the variable end point was determined to be at 5 seconds.

For the 300 mg/dL sample, the values for $C_t'$ remained above 1% from the initiation time point until the end of the testing period, 30 seconds after the initiation time point. Therefore, according to the proviso in the method of the invention, the variable end point was determined to be at 30 seconds after the initiation time point, yielding a glucose concentration measurement of 310 mg/dL. Similarly, the variable end point for the 500 mg/dL sample was also at 30 seconds, yielding a glucose concentration measurement of 505 mg/dL.

EXAMPLE III

Comparison of Results from the Method of the Present Invention with Those from a Method used in the Prior Art The following example compares the results obtained by using the measurement method of the invention with the results from a method used in the prior art.

Eight samples, each containing approximately 350 mg/dL glucose, were prepared and reacted as described in Example I.A. The K/S ratios of each reaction were measured and plotted over time as also described in Example I.A. The same data from each reaction were evaluated according to two different methods to compare the methods.

First, the initiation time point was determined for each of the reactions by detecting an initial drop in the reflectance of at least 10%. As discussed above, this initial drop is partly due to wetting of the test surface, and may not accurately reflect the start of the chemical reaction. The K/S ratio was then measured 18 seconds after the initiation time point determined by this method. The average K/S ratio was 2.46, with a standard deviation of 0.118. The coefficient of variation (the standard deviation divided by the mean) for the 8 samples was 4.8%.

Second, the initiation time point was determined according to the initiation method of the invention for the same data. The K/S value was then measured 17 seconds after the initiation time point. The 17 second time point was selected to enable comparison of the two methods when the average endpoint K/S values were the same value. When using the initiation method of the invention, the average endpoint K/S ratio was also 2.46, but there was significantly less variability between the individual endpoint K/S values: the standard deviation was only 0.075 and the coefficient of variation was only 3.0%. Thus, the initiation method of the invention provides more consistent endpoint values for K/S, which in turn can provide more consistent glucose measurements for patients.

Although the invention has been described with reference to the disclosed embodiments, it should be understood that various modifications can be made without departing from the spirit of the invention. Accordingly, the invention is limited only by the following claims.

We claim:

1. A method of using a reflectance-reading device to determine an initiation time point for measuring a chemical reaction of an analyte from a biological liquid sample on a test surface, comprising the steps of (a) using a device to read a reflectance R of a test surface at a plurality of time points, (b) calculating a K/S ratio of the test surface at each time point according to an equation $$K/S = (1-R)^2/2R$$

(c) monitoring a rate of change of the K/S ratio with respect to time, and (d) determining an initiation time point for measuring a chemical reaction when the rate of change of the K/S ratio is maximal.

2. The method of claim 1, wherein the analyte is glucose.

3. The method of claim 1, wherein the analyte is glycated protein.

4. The method of claim 3, wherein the analyte is fructosamine.

5. A method of using a reflectance-reading device to measure the concentration of an analyte on a test surface, comprising the steps of (a) determining an initiation time point according to the method of claim 1, and (b) measuring the concentration of an analyte at a variable end point, wherein the variable end point is determined by the steps comprising of (1) using a device to read a reflectance R of a test surface at a plurality of time points, (2) calculating a K/S ratio from R at each time point, (3) calculating a concentration parameter corresponding to the K/S ratio at each time point, (4) monitoring a rate of change of the concentration parameter with respect to time, (5) comparing the rate of change of the concentration parameter against a threshold value, and (6) determining the variable end point to be the time at which the rate of change of the concentration parameter is less than the threshold value, with the proviso that during a testing period that began at the initiation time point, if the rate of change of the concentration parameter is never less than the threshold value, then the variable end point is determined to be the end of the testing period.

6. The method of claim 5, wherein subject to the proviso, the variable end point is determined to be the time at which the rate of change of the concentration parameter is less than the threshold value for a plurality of consecutive measurements of the rate of change of the concentration parameter.

7. The method of claim 6, wherein the number of consecutive measurements of the rate of change of the concentration parameter is 2.

8. The method of claim 5, wherein the analyte is glucose.

9. The method of claim 5, wherein the testing period is about 30 seconds.

10. The method of claim 5, wherein the threshold value is about 1% change of concentration parameter per second.

11. A method of using a reflectance-reading device to measure the concentration of an analyte on a test surface, comprising the steps of (a) determining an initiation time point according to the method of claim 1, and (b) measuring the concentration of an analyte at a variable end point, wherein the variable end point is determined by the steps comprising of (1) using a device to read a reflectance R of a test surface at a plurality of time points, (2) calculating a K/S ratio from R at each time point, (3) monitoring a rate of change of the K/S ratio with respect to time, (4) comparing the rate of change of the K/S ratio against a threshold value, and (5) determining the variable end point to be the time at which the rate of change of the K/S ratio is less than the threshold value, with the proviso that during a testing period that began at the initiation time point, if the rate of change of the K/S ratio is never less than the threshold value, then the variable end point is determined to be the end of the testing period.

12. The method of claim 11, wherein subject to the proviso, the variable end point is determined to be the time at which the rate of change of the K/S ratio is less than the threshold value for a plurality of consecutive measurements of the rate of change of the K/S ratio.

13. The method claim 12, wherein the number of consecutive measurements of the rate of change of the K/S ratio is 2.

14. The method of claim 11, wherein the analyte is glucose.

15. The method of claim 11, wherein the testing period is about 30 seconds.

16. The method of claim 11, wherein the threshold value is about 1% change of K/S ratio per second.

* * * * *